United States Patent [19]

Myers

[11] Patent Number: 4,525,842
[45] Date of Patent: Jun. 25, 1985

[54] LASER DEVICE AND METHOD

[76] Inventor: John D. Myers, 900 Sandalwood East, Perrysburg, Ohio 43551

[21] Appl. No.: 583,504

[22] Filed: Feb. 24, 1984

[51] Int. Cl.³ .............................................. H01S 3/08
[52] U.S. Cl. ...................... 372/92; 372/25; 372/11; 372/61; 372/65; 372/40
[58] Field of Search .................... 372/25, 39–41, 372/10, 61, 65, 92, 11, 12

[56] References Cited

U.S. PATENT DOCUMENTS

| | | | |
|---|---|---|---|
| 3,500,238 | 3/1970 | Bazinet, Jr. et al. | 372/40 |
| 3,626,319 | 12/1971 | Young | 372/40 |
| 3,805,186 | 4/1974 | Woodcock | 372/40 |

Primary Examiner—William L. Sikes
Assistant Examiner—Scott, Jr. Léon
Attorney, Agent, or Firm—Cullen, Sloman, Cantor, Grauer, Scott and Rutherford

[57] ABSTRACT

A simplified, relatively inexpensive laser device, wherein the laser elements are fixed in a body exoskeleton of electrical insulating material having a low coefficient of thermal expansion. The preferred embodiment includes a shotgun type laser filter having parallel bores which receive the laser flashlamp and laser rod in fixed relation in a body chamber. The reflector surrounds the laser filter and retains the filter within the body chamber. In the preferred method of this invention, several controlled lasing pulses are generated with each illumination pulse of the flashlamp, substantially increasing the efficiency of the laser device. The number of pulses is generally controlled by increasing the voltage to the flashlamp. The rapid multiple lasing pulses generate an elongated plasma in a fluid medium, such as the vitreous fluid body of an eye which makes the laser device extemely efficient for treating glaucoma and other medical treatments.

23 Claims, 7 Drawing Figures

LASER DEVICE AND METHOD

FIELD AND BACKGROUND OF INVENTION

The present invention relates to laser devices, more particularly passively Q-switched laser devices, a method of generating controlled multiple lasing pulses with each illumination pulse of the laser flashlamp and a method of treatment using very high frequency lasing pulses.

Passively Q-switched laser devices have been known and used for several years. Such laser devices include a dye Q-switch, which is normally partially absorptive, aligned with its optical axis aligned with the laser rod and which serves as a gate, wherein the partial absorption bleaches when the lasing energy level reached a predetermined magnitude. Passively Q-switched laser devices have a substantial advantage over conventional multi-pulsed lasers, which require either that the laser be activated by applying a power in a repeated manner or by shuttering the laser output with a rapidly oscillating shutter, such as electro-optic switches, rotating mirrors or other active devices. A Q-switched laser device emits a series of identical lasing pulses which can be controlled in number from a single pulse to as many as 10 pulses.

Further, there are several types of commercially available lasers, including argon, ruby, carbon dioxide, krypton and neodymium doped glass end YAG laser rods. YAG lasers are preferred in certain medical applications because the YAG laser easily produces a short energy pulse with a high peak power. In medical applications, the laser rips electrons from the target atoms, leading to ionization of the tissue. YAG lasers have been utilized in the treatment of glaucoma, particularly after insertion of an artifical lens, wherein the lens becomes opaque, obscuring vision. The plasma created at the point of focus of the laser produces a shock wave which can be used to cut the opaque membrane at the back surface of the lens, within the vitreous fluid body of the eye, providing a noninvasive cutting procedure. Care, however, must be taken to focus the laser in such a manner to cut the opaque membrane and not damage the adjacent lens. The cutting plasma, generally described as a "microplasma", must therefore be of small size, approximately 50 microns, to limit the cutting to the desired area. The life of the plasma created by a single laser Q-switch pulse is approximately 20 to 200 microseconds at atmosphere pressure, such as found in the human eye. The size of the plasma and, therefore, the shock wave is determined by the energy of the laser pulse. Therefore, for a given Q-switch laser pulse, a given laser plasma size will result. In a conventional multi-pulsed laser, even a Q-switched laser, it is not possible to sustain the plasma created because the frequency of the pulses is greater than the life of the plasma created by a single laser pulse.

It is also desirable to increase the pulse repetition frequency of other multi-pulsed lasers, if the frequency can be increased without substantially increasing the energy required or the expense of the laser device. A more rapidly pulsing laser device would have many applications, including medical applications, such as opthomology, dermatology, microbiology and the like, and scientific applications, including ionization, spectrometry, spectryoscpy, etc. It is not possible, however, to substantially increase the frequency of conventional multi-pulsed lasers without substantially increasing the cost and reducing the reliability of the system. Finally, the cost and reliability of conventional laser systems have limited the applications for such lasers.

Many improvements have been made in lasers in recent years, including the development of athermal laser glass, the passively Q-switched lasers described above, and improvements in the laser components. It will be understood, however, that a laser is made up of several components which must be accurately aligned and which are easily damaged or misaligned. Further, laser systems remain relatively large and expensive. The need therefore remains for a more reliable, less expensive laser device, preferably a laser device wherein the components are permanently aligned and sealed. As described hereinbelow, the laser device of this invention permanently aligns the components of the laser system in a small package, which is more durable and less expensive than the laser devices of the prior art. Further, the laser device and method of this invention substantially increases the frequency of the pulses of the laser device, without increasing the expense or reducing the reliability of the system.

SUMMARY OF THE INVENTION

The preferred embodiment of the laser device of this invention has a body member preferably formed of an electrical insulating material having a low coefficient of thermal expansion and forming an exoskeleton for the laser device. The body member permanently aligns the laser components and protects and seals the system. The body member includes an elongated chamber, which receives the flashlamp and an elongated laser rod fixed in generally parallel relation. A reflector preferably surrounds the flashlamp and laser rod. A front laser mirror is secured to the body member at one end of the chamber and a back laser mirror is secured to the body member, at the opposed end of the chamber, with the mirrors permanently aligned by the body member.

As described, the preferred embodiment of the laser device of this invention is a passively Q-switch laser, wherein a dye Q-switch is located between the laser rod and one of said laser mirrors, and the body member chamber is filled with an inert gas. In the most preferred embodiment of the invention, the laser flashlamp and laser rod are secured within the body member chamber in a laser filter having parallel elongated bores extending generally perpendicular to the reflective surfaces of the laser mirrors. This "shotgun" type of laser filter is preferably oval-shaped in cross section and the body member chamber or bore is similarly oval-shaped. The reflector is preferably a powdered material, such as powdered barium sulfate, which is packed around the laser filter, securely retaining the laser filter against any movement in the body member chamber.

The laser device includes a source of pulsing electric energy or voltage, which may be supplied by a simple capacitance circuit connected to the input of the flashlamp. In normal operation, the pulsed voltage to the flashlamp illuminates the flashlamp and energizes the laser rod. As will be understood by those skilled in the art, the laser rod includes an active element, such as neodimium YAG. The laser rod then stores energy in proportion to the flashlamp illumination, and the laser device emits a single laser pulse when the gain of the laser rod exceeds the losses of the Q-switch and mirrors. The dye of the Q-switch is normally absorptive, however, when the energy stored in the laser rod reaches a predetermined value, the Q-switch bleaches and the laser rod emits a single pulse. The Q-switch thus serves as a gate and the laser device emits one laser pulse with each illumination of the flashlamp.

It has been discovered by the applicant, however, that it is possible to generate several lasing pulses of approximately equal magnitude, with each illumination pulse of the flashlamp, in a laser device of the type disclosed herein by "balancing" the laser components. Further, it has been discovered that the number of additional lasing pulses may be accurately controlled by increasing the voltage to the flashlamp in staged increments. It was previously understood that lasers sometimes emitted spurious lasing discharges, however, it has now been discovered that it is possible to control the pulsed voltage sufficiently to repeatedly generate gain in the laser rod, thereby generating controlled multiple lasing pulses with each flashlamp illumination pulse, substantially increasing the efficiency of the laser device and the number of the laser pulses emitted.

In the disclosed embodiments of the laser device of this invention having an elongated laser rod, multiple lasing pulses are emitted by the lasing device when the volume of the laser rod in cubic millimeters multiplied by the electric energy transmitted to the flashlamp in Joules exceeds about 4,000. For example, a YAG laser rod having a diameter of 4 mm and a length of 75 mm has a volume of 942 mm$^3$. When the input voltage to the flashlamp is 515 volts or 5.3 Joules, a single pulse is emitted by the laser rod. When the voltage is increased to 580 volts or 6.7 Joules, two pulses of substantially equal magnitude are emitted by the laser rod. At a voltage of 635 volts or 8.1 Joules, three pulses are emitted by the laser rod, etc., wherein the addition of about 1.4 Joules adds one laser pulse per flashlamp illumination pulse. This unexpected result has many advantages in medical and scientific applications for lasers. As described above, several attempts have been made to increase the number and frequency of laser pulses, including complex shutter devices, rotating mirrors and the like. The disclosed method of increasing the number and frequency of the laser pulses, however, is passive and does not require any moving elements. It will be understood, however, that the other lasing components must also be balanced to achieve multiple lasing pulses. For example, in the embodiment of the laser device described above, the front mirror preferably has a reflectivity of 20 to 75% and the Q-switch includes a 0.15 to 0.45 optical density dye.

Although many applications of the multiple lasing device or pulsetrain laser of this invention could be described, the method of treatment of opacity of the eye lens resulting from glaucoma and the like has unexpected advantages. As described above, laser devices are being used to treat glaucoma, wherein a pulsing laser is focused on the foreign material at the back surface or anterior of the lens, within the vitreous fluid body of the eye. In single pulse lasers, however, it is not possible to maintain the microplasma, because the life of the microplasma is less than the times between adjacent pulses of the laser. With the multiple pulse laser of this invention, however, it is possible to selectively add to the laser energy of the microplasma and thereby increase the life of the plasma. The laser plasma actually grows from the focal point of the laser, backwards toward the laser, reducing the likelihood of damage to the lens and improving the accuracy and efficiency of the method of treatment. The method of treatment thus preferably includes generating a single lasing pulse focused within the eye vitreous fluid, and spaced from the lens back surface. The number and frequency of the lasing pulses is then increased to generate an elongated lasing plasma within the eye vitreous fluid, moving toward the back surface of the lens, until the lasing plasma contacts and destroys the foreign matter.

Other advantages and meritorious features of this invention will be more fully understood from the following description of the preferred embodiments and method of this invention, the appended claims and the drawings, a brief description of which follows.

DESCRIPTION OF THE PREFERRED EMBODIMENTS AND METHOD

Figures 1, 2, 3, 4:
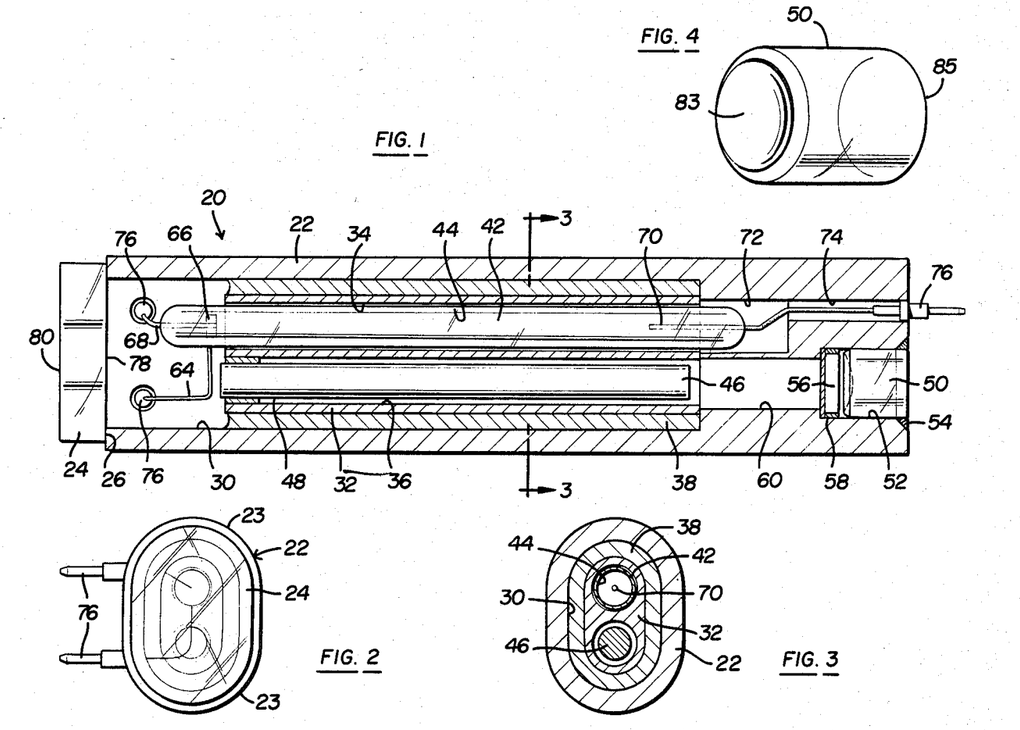
FIG. 1 is a partially cross-sectioned side view of one embodiment of the laser device of this invention.
FIG. 2 is an end-view of the laser device shown in FIG. 1 through mirror 24.
FIG. 3 is an end cross-sectional view of the laser device shown in FIG. 1, in the direction of view arrows 3—3.
FIG. 4 is an enlarged perspective view of the rear or back laser mirror shown in FIG. 1.

The embodiment of the laser device 20 shown in the drawings is relatively small and compact, and all of the components of the laser device are permanently aligned. These advantages are provided by the unique laser body member 22 which forms the exoskeleton of the laser device and functions as the optical supporting structure of the laser. In the preferred embodiment, therefore, the side surfaces 23 of the body member are radiused as shown in FIG. 2.

Figures 5, 6:
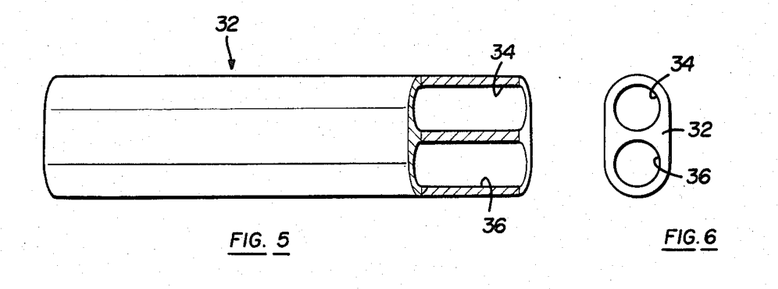
FIG. 5 is a side view, partially cross-sectioned of the laser filter shown in FIG. 1.
FIG. 6 is an end view of the laser filter shown in FIG. 5.

The front laser mirror 24 is permanently attached to one end of the body member by epoxy 26 or other suitable fastening means. The body member 22 includes a cavity or primary bore 30, which is sealed by the front laser mirror 24. Inside the body member cavity is an elongated laser filter member 32 having parallel bores 34 and 36, as best shown in FIGS. 5 and 6. The laser filter member is permanently aligned and secured within the body chamber by laser reflector material 38, as will be described more fully herein below. The laser flashlamp 42 is permanently aligned in one bore 34 of the laser filter 32 by resin 44 or other suitable means. The laser rod 46 is secured in the other filter member bore 36 by resin 48 or other suitable means. As will be understood, therefore, the laser rod 46 and flashlamp 42 are permanently aligned in parallel relation and the longitudinal axis of the elongated laser rod is generally perpendicular to the reflective surface of the front mirror 24.

The back or rear laser mirror 50 is permanently aligned in a cylindrical bore 52 at the rear of the laser body 22, with the longitudinal axis of the rear mirror 50 coaxillaly aligned with the longitudinal axis of the laser rod 46. The rear mirror 50 is permanently aligned and sealed in the cylindrical bore 52 by resin 54 or other suitable means. The disc shaped Q-switch 56 is retained by an annular ferrule 58 in bore 52 axially aligned with the rear laser mirror 50 of the laser rod 46. A cylindrical counterbore 60 in the laser body, having a diameter approximately equal to the bore 36 in the laser filter, provides communication between the laser rod 46, the Q-switch 56 and the rear laser mirror 50.

Having described the general layout of the components of the laser device 20, a more detailed description of the preferred embodiments of the laser components may now be provided. As described, the laser body member 22 forms the exoskeleton of the laser device and permanently aligns the components. Thus, the body should be formed of an electrical insulating material, preferably having a low coefficient of thermal expansion, because the laser mirrors are permanently bonded to the body. Thus, the body is preferably formed from an impervious silicate material, such as "Martite", which is an aluminum silicate material commercially available from Kigere, Inc. of Toledo, Ohio. Other suitable materials include "Macor", available from Corning Glass Works and alumina tubing. The laser body is preferably cast as an integral unit and thereafter machined. In the preferred embodiment, the laser body cavity 30 is evacuated through pin holes, not shown, after completion of the assembly. The body cavity is then back filled with an inert gas, such as nitrogen, and the pin holes are sealed.

The laser filter 32 is a "shotgun" type filter having parallel cylindrical bores 34 and 36, which receive and secure the flashlamp 42 and laser rod 46, as described above. A suitable material for the filter tube is KSF-5 available from Kigere, Inc. which is lithia alumina silicate glass doped with samarum, preferably about 5%. As will be understood by those skilled in the art, the preferred material for the laser filter will depend upon the laser system and other suitable materials may be used. A shotgun type filter is preferred in the present embodiment to securely retain and permanently align the flashlamp 42 and laser rod 46, as now described. The filter tube 32 is secured in permanent alignment in the laser body cavity 30 by reflector material 38. In the preferred embodiment of the laser device, the laser reflector 38 is a powdered material, such as powdered barium sulphate, which is packed between the inside surface of the body member cavity 30 and the outside surface of the shotgun laser filter 32, permanently aligning the flashlamp 42 and laser rod 46. A conventional bonding material may be added to the powdered barium sulphate.

The flashlamp 42 is a conventional flashlamp such as the flashlamps available from ILC Technologies of Sunnyvale, Calif. Other suitable flashlamps are available from Siemens Laboratories. It will be understood that the preferred arch length of the flashlamp will be dependent upon the size and type of laser rod used in the assembly. In the disclosed embodiment, an arc length of between 60 and 75 mm is preferred. As will be understood by those skilled in the art, the flashlamp includes a trigger wire 64, which is connected to a source of pulsing voltage, which triggers the illumination of the flashlamp. The trigger wire 64 is connected to the cathode 66 of the flashlamp, which is also connected to ground wire 68. In the disclosed embodiment, the opposite end of the flashlamp includes a anode wire 70 and the wires 64, 68 and 70 are connected to the electrical circuit of the laser device by conventional connectors 76. As will be understood by those skilled in the art, any source of pulsating voltage may be applied to the trigger wire 64. The simplest form is a capacitor discharge which pulses through a coil to produce a voltage of about 10 kilovolts having a frequency of about 120 microseconds.

The preferred laser rod 46 will be dependent upon the function or purpose of the laser device 20. In the preferred passively Q-switched laser device capable of generating controlled multiple lasing pulses, or pulse-train laser device of this invention, the laser rod 46 is preferably formed from a conventional YAG (yttrium-aluminum-garnet) laser material. Other suitable materials for the laser rod include "Q 100" laser glass available from Kigre, Inc., and described in U.S. Pat. No. 4,333,848. Q-100 is an athermal phosphate laser glass doped with $Nd_2O_3$ as the laseable component. It is also possible to achieve a pulse-train effect with other laser materials, including other glass or crystaline lasers, such as ruby lasers, and other laser systems. As will be described more fully hereinbelow, it is necessary to balance the laser components to achieve multiple lasing pulses with each illumination pulse of the flashlamp. Thus, the volume of the laser rod 46 is critical to achieving the desired pulse train effect. The disclosed embodiment of the laser rod is a cylindrical YAG laser rod having a diameter of 4 mm, a length of 75 mm and a volume of 945 $mm^3$.

The front laser mirror 24 is a conventional plano-plano laser mirror, which may be formed of any conventional standard optical glass, such as BK7 available from Schott Optical Glass, Inc. The inside surface 78 of the front laser mirror preferably has a reflectivity of about 10 to 55%. In the preferred embodiment of the pulse-train-laser device of this invention, the reflectivity of the inside surface 78 of the front laser mirror is between 30 and 40%. The outside surface 80 includes a conventional multilayer AR (antireflective) coating. As described, the front mirror is permanently bonded and aligned to the forward end of the laser body member 22 by epoxy 26 or other suitable fastening means. The rear or back mirror 50 may also be formed of any standard optical glass, such as BK7 available from Schott Optical Glass, Inc. The inside surface 83 (see FIG. 4) may be either concave, having a radius between 3 to 10 mm, or planar, depending upon the beam divergence desired. The inside surface is coated to reflect the maximum reflectivity at the wave length of the laser. For low beam divergence, from 1 to 3 milliradans, a concave radius of between 3 and 6 meters is desirable. Larger beamed divergences are obtainable using a back laser mirror with a concave radius of curvature of between 7 and 10 meters, or a planar surface. The back surface 85 of the rear laser mirror 50 is polished, planar and clear. It should be noted that it is possible to interchange the front and rear mirrors, which will not affect the operation of the laser device, except to cause the laser output to emit from the opposite end. As described, the real laser mirror 50 is permanently bonded and aligned in the cylindrical bore 52 in the laser body by epoxy 54 or other fastening means.

The disclosed dye Q-switch is available from Eastman Kodak, wherein the dye is BIS (4-Di Methylaminodith 10 Benzil) (nickel) in a cellulose matrix. The Q-switch is available in sheet form of optical quality. It will be understood by those skilled in the art, the dye bleaches at a predetermined leasing energy, providing a passive pulsing laser gate.

Having described the embodiment of laser device 20 and the preferred embodiments of the laser components disclosed in the drawings, it is now possible to describe the operation of the laser device and the preferred method of generating multiple lasing pulses with each illumination pulse of the flashlamp, referred to herein as a pulse-train laser or effect. As will be understood by those skilled in the art, the flashlamp 42 will provide an illumination pulse with each voltage pulse transmitted through trigger wire 64 to the flashlamp cathode 66. The illumination pulse of the flashlamp is transmitted through the laser filter 32 to the laser rod 46. The laser filter 32 filters the illumination received by the laser rod, limiting the illumination to the desired frequency. The illumination of the laser rod excites the lasable component of the laser rod. The laser rod then emits a laser pulse, which is reflected by the inside reflective surfaces of the laser mirror 24 and 50 through the Q-switch 56. As will be understood, the laser rod stores energy in proportion to the flashlamp illumination, and the laser device emits a single laser pulse when the gain of the laser rod exceeds the losses of the Q-switch and the mirrors. It has now been discovered that it is possible to achieve multiple lasing pulses with each illumination pulse of the flashlamp, or a pulse-train laser effect, when the pulsed voltage is sufficient to repeatedly generate gain in the laser rod with each illumination pulse. As described above, however, it is necessary to balance the components of the laser device to achieve a pulse-train effect.

To achieve controlled multiple lasing pulses, the volume of the laser rod must be sufficiently great to store sufficient energy in the laser rod to achieve multiple lasing pulses. As described, it was previously recognized that lasers sometimes emit suprious or unwanted discharges, however, the prior art did not recognize that it is possible to generate several multiple lasing pulses of approximately equal magnitude with each illumination pulse. Further, the number and frequency of the lasing pulses can be accurately controlled by increasing the energy supplied to the flashlamp. Finally, it has been discovered that the number of lasing pulses emitted by the laser device with each flashlamp illumination pulse is a linear function of the energy input to the flashlamp, as will now be described.

In a passively Q-switched laser device of the type described hereinabove, wherein the front mirror has a reflectivity of about 20 to 75% and the Q-switch has an optical dye density of 0.15 to 0.45, it is possible to generate controlled multiple lasing pulses using a YAG laser rod, wherein the rod size is 4 mm×75 mm, having a volume of 942 mm³. Based upon experiments with YAG laser rods, the critical volume of the laser rod appears to be about 650 to 800 mm³. For example, a 3 mm×30 mm YAG laser rod will not produce consistent multiple pulses having substantially equal energy. By increasing the voltage to the flashlamp, thereby increasing the energy input into the laser rod, it is possible to achieve two or three lasing pulses with each flashlamp illumination pulse, however more than about three lasing pulses cannot be obtained no matter how much additional energy is supplied to the laser rod. Generally, the same result was found utilizing a 4 mm×50 mm YAG laser rod. By increasing the size and volume of the laser rod to 4 mm×75 mm, controlled multiple lasing pulses were achieved, up to about 10 lasing pulses with each flashlamp illumination pulse.

Provided the volume of the laser rod is greater than the minimum critical volume, as described above, the number of lasing pulses achieved with each flashlamp pulse is dependent upon the energy input into the flashlamp. Actual tests established that the number of lasing pulses is a linear function of the energy input to the flashlamp by the following equation:

Energy input to the flashlamp in Joules $= \frac{1}{2}CV^2$ wherein C is the capacitance of the laser rod in microfarads and V is the voltage in kilovolts. Thus, for example, with a capacitance of 40 microfarads, an input of 500 volts stores 5 Joules in the laser rod capicator and an input oif 600 volts stores 7.2 Joules.

The following table establishes the linear relation between the energy input to the flashlamp and the number of lasing pulses generated by the lasing device with each flashlamp illumination. The laser used to obtain this data was the laser device described above using a 4 mm×75 mm YAG laser rod.

| Volts | Energy Input To Flashlamp | No. Pulses Emitted | Total Energy In All Pulses |
|---|---|---|---|
| 515 | 5.3 Joules | 1 | 25 Millijoules |
| 580 | 6.7 Joules | 2 | 50 Millijoules |
| 635 | 8.1 Joules | 3 | 84 Millijoules |
| 685 | 9.5 Joules | 4 | 104 Millijoules |
| 730 | 10.7 Joules | 5 | 130 Millijoules |
| 780 | 12.1 Joules | 6 | 155 Millijoules |

Each of the Q-switched lasing pulses emitted was approximately identical in pulse width and energy. The pulse widths were between 7 and 12 nanoseconds in duration and each pulse contained between 22 and 28 millijoules of energy. Further, the beam divergence of each of the lasing pulses was between 1 and 3 milliradians.

It will be noted from the Table above that the number of lasing pulses is substantially straight or a linear function of the energy input to the laser rod. For example, the addition of approximately 1.4 Joules energy increases the number of lasing pulses emitted by the laser device from 2 to 3, 3 to 4, etc. Further, the energy of each multiple lasing pulse was substantially identical. Thus, the disclosed method of generating multiple lasing pulses is extremely efficient. Finally, it is possible to generate lasing pulses of substantially equal magnitude at very high frequencies using a passively Q-switched lasing device, which is not possible with the present state-of-the-art.

Having described the operation of the preferred laser device, the method of this invention includes applying a pulsed voltage to the laser flashlamp 42 to illuminate the flashlamp and energize the laser rod 46. The laser rod stores energy in proportion to the energy in the flashlamp illumination. The laser device 20 will then emit a single laser pulse through the front mirror 24 when the gain of the laser rod exceeds the losses of the Q-switch and the laser mirrors. The laser device will generate controlled multiple lasing pulses with each flashlamp illumination pulse when the pulsed voltage is sufficient to repeatedly generate gain in the laser rod. As described, the preferred pulse-train laser device and method of generating controlled multiple lasing pulses of this invention has many applications, including medical applications, such as opthomalogy, etc and scientific applications, including ionization, spectromatry and spectroscopy. It will be understood, for example, that pulsing lasers utilized to determine the location of and distance to a moving object will be more accurate where the frequency of the lasing pulses is increased. It has been discovered, however, that the pulse-train laser and method of generating multiple lasing pulses has a very unique advantage in vitreous fluids, such as in the treatment of opacity of the human eye resulting from glaucoma or other diseases of the eye, as described below.

It is known that a laser creates a plasma in a fluid medium which is transparent to the laser wavelength, such as the vitreous fluid body of the human eye. Lasers are thus used to treat glaucoma and similar ailments of the eye. In glaucoma cases, particularly after insertion of an artifical lens, the posterior lens capsule sometimes becomes opaque, obscuring vision. It has been established that the laser plasma, created at the point of focus of a Q-switched laser, can be utilized to cut the opaque membrane which obscures the patient's vision. This non-invasive laser cutting procedure permits the posterior lens to part, thereby permitting light to enter the eye. Care must be taken, however, to focus the laser to avoid damage to the adjacent artifical lens, limiting the laser cut to the opaque membrane. The cutting plasma, referred to as a microplasma, must therefore be relatively small, approximately 50 microns, to limit the laser cutting to the desired area.

Figure 7:
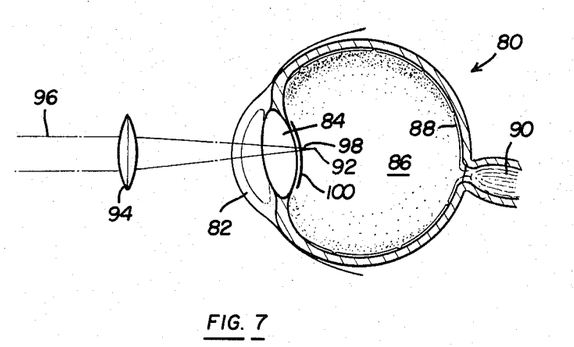
FIG. 7 is the cross section of a human eye showing a method of treatment with a multiple pulse or pulse-train laser device.

Experiments have determined that the life of the microplasma created by a single Q-switched laser pulse is approximately between 20 and 200 microseconds at atmospheric pressure, such as found in the vitreous fluid body of the human eye. The size of the plasma is determined by the energy in the laser pulse. Therefore, for a given Q-switched laser pulse, a given laser plasma size will result depending upon the optical system. A laser microplasma appears as a small illuminated dot. It has been discovered, however, using the pulse-train laser of this invention, that where the frequency of the laser pulses is equal to or greater than the life of the microplasma, the microplasma will not extinguish, but will be rekindled for an additional time period. That is, where the frequency of the laser pulses are sufficiently close, such that each succeeding laser pulse arrives at the focus of the laser during the microplasma lifetime, the plasma does not extinguish. The result is a plasma having a size which is characteristic of the energy of a single pulse, but having a cutting power which is characteristic of a plasma generated by a single laser pulse of much larger energy; typically of the order of the energy per pulse multiplied by the number of pulses in the pulse train. Thus, with a multiple pulse train laser, as described above, it is possible to selectively add to the energy and increase the life of the plasma. Further, it has been discovered that the microplasma actually "grows" from the focal point of the laser, backwards toward the laser device. As described, a single laser pulse creates a microplasma which appears as a small illuminated dot. At two pulses, the microplasma becomes oblong, and at three or more pulses, the plasma becomes an elongated stream, moving toward the laser device. Using the pulse-train laser of this invention, it is therefore possible to focus the laser within the vitreous fluid body of the eye and then back up the plasma to the back of the lens and touch the posterior lens capsule, as shown in FIG. 7, wherein 80 is the cross section of a human eye having a cornea 82, a lens 84 and a vitreous fluid body 86. The retina is shown at 88 and the optic nerve is located generally opposite the lens 84 at 90. It will be understood that all lasers work by the generation of light energy. The energy density is a maximum near the point of focus, but tissue just anterior or posterior to the point of focus can also be ionized. As described, therefore, it is very important to focus the laser in the vitreous fluid body of the eye, away from the retina, 88 and the lens 84.

Using the pulse-train laser of this invention, the laser is focused at a point 92, spaced from the anterior surface of the lens 84, by a conventional lens 94. The laser pulses from the laser device are represented by the dashed line 96, which is exaggerated for clarity. The lens 94 focuses the cylindrical laser pulses 96, preferably to a cone angle of about 16 degrees, to avoid damage to the cornea 82 and lens 84. Once the focus point 94 has been established by setting the pulse-train laser device to emit a single lasing pulse, the voltage to the flashlamp is increased to generate the laser pulse train effect, creating an elongated plasma or plasma stream 98, which backs up toward the laser device and the anterior surface of the lens 84. When the plasma stream 98 touches the glaucoma membrane 100, the membrane is ionized or destroyed, clearing the vision through the lens 84.

The method of treatment of opacity of the lens resulting from foreign matter at the back or anterior surface of the lens therefore includes generating a single lasing pulse emitted from the laser device to establish the point of focus 92 within the eye vitreous fluid body 86, spaced from the anterior surface of the lens 84. The method then includes increasing the frequency of the lasing pulses to generate an elongate lasing plasma or pulse stream 98 within the eye vitreous fluid, moving from the point of focus 92 toward the anterior surface of the lens 84, until the lasing plasma contacts and destroys the foreign matter 100.

Having described the preferred embodiments of the laser device, including the preferred embodiments of the pulse-train laser of this invention, the method of generating controlled multiple lasing pulses of substantially equal magnitude and a method of treatment using a pulse-train laser, it will be understood that various modifications may be made to the laser device within the purview of the appended claims. For example, other pulse-train laser devices may be utilized to remove foreign matter in vitreous fluids, provided the frequency of the pulsing laser is sufficient to create a plasma stream, as described. Further, the components of the laser device may be modified as desired for a particular application. It will also be understood that the laser components may be separately utilized and aligned to achieve a pulse-train laser. However, the disclosed embodiment of the laser device having a body member which forms the exoskeleton has may separate advantages as described above. Finally, the specifically disclosed laser device 20, including the body member exoskeleton, may be utilized in conventional laser devices providing the advantages of permanent alignment, reduction in size and reliability.

Having described the laser device and methods of this invention, I now claim the invention as follows:

1. A laser device, comprising:
a body member formed of an electrical insulating material having a low coefficient of thermal expansion and forming an exoskeleton for said laser device, said body member having an internal chamber opening through its opposed ends, a front laser mirror permanently attached to one of said body member ends sealing said one end, a laser filter within said body member chamber having elongated parallel bores extending generally perpendicularly to the reflective surface of said front laser mirror, a laser reflector surrounding said laser filter within said body chamber permanently aligning said filter within said chamber, a laser flashlamp located within one of said laser filter bores and permanently aligned therein and an elongated laser rod located within the other of said laser filter bores permanently aligned therein, and a back laser mirror aligned with said laser rod having a reflective surface generally perpendicular to the longitudinal axis of said laser rod, said back laser mirror permanently attached to the opposed end of said body member, opposite said front laser mirror, sealed in said opposed body member end, said body member thus providing a sealed construction with the laser elements in fixed permanent alignment.

2. The laser device defined in claim 1, characterized in that said laser device includes a dye Q-switch located between said laser rod and one of said laser mirrors, and a source of pulsing electrical energy connected to said flashlamp, the volume of said laser rod and the pulsed electrical energy to said flashlamp being sufficient to repeatedly generate gain in said laser rod, with each electrical pulse to said flashlamp generating controlled multiple laser pulses of substanntially equal magnitude.

3. The laser device defined in claim 2, characterized in that said laser rod has a volume of greater than about 650 mm$^3$ and the pulsing electrical energy to said flashlamp is greater than about 7 Joules.

4. The laser device defined in claim 3, characterized in that said dye Q-switch has an optical density of 0.15 to 0.45% and said front mirror has 20 to 75% reflectivity.

5. The laser device defined in claim 1, characterized in that said laser reflector is powdered barium sulfate packed between said filter and the internal wall of said body member internal chamber.

6. The laser device defined in claim 1, characterized in that said laser body member chamber is filled with a non-oxydizing gas.

7. The laser device defined in claim 1, characterized in that a laser Q-switch is positioned in fixed relation in said chamber between said laser rod and one of said mirrors.

8. The laser device defined in claim 1, characterized in that said front laser mirror is plano-plano having a reflectivity of about 30 to 55% and the surface of said back mirror adjacent said laser rod is concave.

9. A passively Q-switched laser device, comprising: a body member formed of an electrical insulating material having a low coefficient of thermal expansion forming an exoskeleton for supporting said laser device in an optical device, said body member having a sealed elongated chamber, one end of said chamber having a front laser mirror and the opposed end having a back laser mirror with said mirrors in sealed relation, and permanently aligned on said body member, a flashlamp and an elongated laser rod fixed in generally parallel relationship to the said flashlamp, within said chamber generally and said laser rod, and a Q-switch located between said laser rod and one of said laser mirrors in fixed relation, and said body member chamber filled with an inert gas.

10. The laser device defined in claim 9, characterized that said body member is an integrally cast body of impervious silicate.

11. The laser device defined in claim 9, including a laser filter located within said body member chamber having generally parallel elongated bores extending generally perpendicular to the reflective surfaces of said laser mirrors, said flashlamp located in fixed permanent relation in one of said laser bores and said laser rod located in fixed relation in the other of said laser bores, and said reflector surrounding said laser filter.

12. The laser device defined in claim 11, characterized in that said reflector is powdered barium sulfate packed between said filter and the internal surface of said body member chamber.

13. The laser device defined in claim 9, characterized in that said laser rod is a YAG laser rod consisting essentially of yttrium-aluminum-garnet.

14. The laser device defined in claim 9, characterized in that said laser device includes a source of pulsing electrical voltage connected to said flashlamp, the volume of said elongated flashlamp in cubic millimeters multiplied by the pulsing electrical energy transmitted to said flashlamp in Joules exceeds about 4,000 and said flashlamp generating controlled multiple lasing pulses with each pulse of said flashlamp.

15. The laser device defined in claim 14, characterized in that said dye Q-switch has an optical density of 0.15 to 0.45% and said front mirror has 20 to 75% reflectivity.

16. A passively Q-switched laser device capable of generating controlled multiple lasing pulses of substantially equal magnitude with each flashlamp pulse, said laser device comprising: an electrical flashlamp, an elongated laser rod in close proximity and generally parallel to said flashlamp, a reflector surrounding said flashlamp and laser rod, front and back laser mirrors having reflective surfaces generally perpendicular to the axis of said laser rod, and a dye Q-switch located between one end of said laser rod and one of said laser mirrors having a dye reflective surface perpendicular to the axis or said laser rod, and a source of pulsing electrical energy connected to said laser rod, the volume of said flashlamp in cubic millimeters multiplied by the pulsing electrical energy transmitted to said flashlamp in Joules exceeding about 4,000 and said pulsing electrical energy sufficient to repeatedly generate gain in said laser rod with each illuminating pulse of said flashlamp to generate controlled multiple lasing pulses of substantially equal magnitude by said laser device with each pulse of electrical energy transmitted to said flashlamp.

17. The passively Q-switched laser device defined in claim 16, characterized in that said dye reflective surface of said Q-switch has an optical density of 0.15 to 0.45% and said front mirror has reflectivity of between about 20 and 75%.

18. The passively Q-switched laser device defined in claim 16, characterized in that said laser device includes an integral filter body having generally parallel elongated bores extending generally perpendicular to the reflective surfaces of said mirrors, said flashlamp and laser rod located in said laser filter bores.

19. A method of generating controlled multiple lasing pulses with each flashlamp pulse of a laser device, said laser device having an electrical flashlamp, an elongated laser rod in close proximity and generally parallel to said flashlamp, a reflector surrounding said flashlamp and laser rod, front and back laser mirrors having a reflective surface generally perpendicular to the axis of said laser rod and a dye Q-switch located between one end of said laser rod and one of said laser mirrors being aligned with the axis of said laser rod, the method comprising:

applying a pulsed electrical voltage to said flashlamp to illuminate said flashlamp and energize said laser rod, said laser rods storing lasing energy in proportion to said flashlamp illumination, said laser device emitting a single laser pulse when the gain of said laser rod exceeds the optical losses of said Q-switch and mirrors, said pulsed voltage sufficient to repeatedly generate gain in said laser rod following said single laser pulse to generate controlled multiple lasing pulses of substantially equal magnitude with each flashlamp illumination pulse.

20. The method of generating controlled multiple lasing pulses as defined in claim 19, wherein said laser rod has a volume of greater than about 800 mm$^3$ and a source of pulsed energy connected to said flashlamp, said method including applying a pulsing voltage through said flashlamp greater than about 7 Joules.

21. The method of generating controlled multiple lasing pulses as defined in claim 19, including generating said controlled multiple lasing pulses in a vitreous fluid medium with the frequency of said lasing pulses sufficient to generate a continuous elongated plasma in said fluid medium.

22. The method of generating controlled multiple lasing pulses as defined in claim 19, including first generating said single lasing pulse in a vitreous fluid medium, then increasing said pulsed voltage to said flashlamp to generate said controlled multiple pulses with each flashlamp illumination pulse, generating a continuous elongated plasma in said fluid medium.

23. The method of generating controlled multiple lasing pulses as defined in claim 22, wherein said fluid medium is the vitreous fluid body of any eye, the method including first generating said single lasing pulse in said eye vitreous body, spaced from the back surface of the eye lens, then increasing said pulsed voltage to said laser flashlamp to generate said continous elongated plasma within aaid eye vitreous fluid body to adjacent said lens back surface to remove foreign matter adjacent said lens.

24. A method of treatment of opacity of the lens of an eye resulting from foreign matter at the back surface of the eye lens within the vitreous fluid body of the eye with a passively Q-switched laser device, the method comprising:
(a) generating a single lasing pulse emitted from said laser device focused within said eye vitreous fluid body, spaced from said lens back surface, creating a microplasma dot in said vitreous fluid body
(b) then increasing the frequency of the lasing pulses emitted from said lasing device having a frequency greater than the life of said microplasma to generate an elongated lasing plasma within said eye vitreous fluid moving toward said lens back surface, until said elongated lasing plasma contacts and destroys said foreign matter.

25. The method of treatment defined in claim 24, wherein said laser device includes a flashlamp, an elongated laser road in close proximity and generally parallel to said laser rod, a reflector surrounding said laser road and flashlamp, front and back laser mirrors on opposed sides of said laser rod each having a reflective surface generally perpendicular to the axis of said laser rod, a Q-switch located between one end of said laser rod and one of said mirrors having a reflective surface generally perpendicular to the axis of said laser rod and a source of controlled pulsing electric voltage connected to said flashlamp, the method including applying said pulsed electric voltage to said flashlamp to illuminate said flashlamp and energize said laser rod, said laser rod storing energy in proportion to said flashlamp illumination, said laser device then emitting a single lasing pulse focused within said eye vitreous fluid body spaced from said lens back surface when the gain of said laser rod exceeds the losses of said Q-switch and mirrors, then increasing the pulsed voltage to said flashlamp sufficiently to repeatedly generate gain in said laser rod to generate controlled multiple lasing pulses with each flashlamp illumination, generating said elongated lasing plasma within said eye vitreous fluid.

26. The method of treatment defined in claim 25, wherein said laser rod has a volume of greater than about 600 mm$^3$, the method then including first generating a single lasing pulse by maintaining the voltage to said flashlamp at less than about 6 Joules, then increasing the voltage to said flashlamp to generate said controlled multiple lasing pulse with each illumination of said flashlamp.

* * * * *

UNITED STATES PATENT OFFICE
CERTIFICATE OF CORRECTION

Patent No. 4,525,842     Dated June 25, 1985

Inventor(s) John D. Myers

It is certified that error appears in the above-identified patent and that said Letters Patent are hereby corrected as shown below:

In claim 23, line 40, delete "aaid" and insert "said".

Cancel claims 24, 25 and 26.

Signed and Sealed this

Eleventh Day of February 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,525,842
DATED : June 25, 1985
INVENTOR(S) : John D. Myers

It is certified that error appears in the above-identified patent and that said Letters Patent is hereby corrected as shown below:

Claim 16, line 39, delete "flashlamp" and insert therefore -- laser rod -- .

Signed and Sealed this

Sixteenth Day of August, 1988

Attest:

DONALD J. QUIGG

Attesting Officer

Commissioner of Patents and Trademarks